United States Patent [19]

Hounsfield

[11] Patent Number: 4,639,941
[45] Date of Patent: * Jan. 27, 1987

[54] RADIOGRAPHY

[75] Inventor: Godfrey N. Hounsfield, Newark, England

[73] Assignee: EMI Limited, Hayes, England

[*] Notice: The portion of the term of this patent subsequent to Dec. 11, 1990 has been disclaimed.

[21] Appl. No.: 609,521

[22] Filed: May 14, 1984

Related U.S. Application Data

[60] Continuation of Ser. No. 13,476, Feb. 21, 1979, Ser. No. 858,612, Dec. 8, 1977, Pat. No. 4,188,541, and Ser. No. 869,711, Jan. 16, 1978, which is a continuation of Ser. No. 758,147, Jan. 10, 1977, abandoned, which is a continuation of Ser. No. 481,443, Jun. 20, 1974, Pat. No. 4,035,647, which is a division of Ser. No. 358,980, May 10, 1973, Pat. No. 3,881,110, said Ser. No. 858,612, is a division of Ser. No. 780,791, Mar. 24, 1977, abandoned, which is a continuation of Ser. No. 657,543, Feb. 12, 1976, Pat. No. 4,052,618, which is a division of Ser. No. 468,005, May 7, 1974, Pat. No. 3,944,833, which is a division of Ser. No. 349,198, Apr. 9, 1973, Pat. No. 3,866,047, which is a continuation-in-part of Ser. No. 212,778, Dec. 27, 1971, Pat. No. 3,778,614, which is a continuation of Ser. No. 861,358, Aug. 21, 1969, abandoned.

[51] Int. Cl.$^4$ ............................................. G01N 23/06
[52] U.S. Cl. ......................................... 378/11; 378/4; 378/9; 378/14; 378/18; 378/19; 378/20; 378/901; 358/111; 364/414
[58] Field of Search .................... 378/7, 19, 4, 6, 9, 378/10–15, 20, 18, 901; 358/111; 382/6; 364/414

[56] References Cited

U.S. PATENT DOCUMENTS

| | | | |
|---|---|---|---|
| 2,281,931 | 11/1942 | Frank | 250/61.5 |
| 3,106,640 | 3/1963 | Oldendorf | 250/52 |
| 3,432,657 | 3/1969 | Slavin | 250/53 |
| 3,449,569 | 6/1969 | Oller | 250/50 |
| 3,670,163 | 6/1972 | Lajus | 250/50 |
| 3,835,323 | 10/1974 | Kahil | 250/360 |
| 3,852,611 | 12/1974 | Cesar | 250/445 |

OTHER PUBLICATIONS

Hounsfield, G. N., "Computerized Transverse Axial Scanning (Tomography): Part I, Description of System," British Journal of Radiology, vol. 46, pp. 1016–1022 (1973).

Takahashi, S. (1957), Rotation Radiography, Japan Society for Promotion of Science, Tokyo.

Takahashi, S. (1969), "An Atlas of Axial Transverse Tomography and Its Clinical Application," Springer Verlag, Berlin.

Cormack, A. M. (1963), "Representation of a Function by Its Line Integrals, With Some Radiological Applications," Journal of Applied Physics 34, 2722–2727.

Cormack, A. M. (1964), "Representation of a Function by Its Line Integrals, With Some Radiological Applications," II Journal of Applied Physics 35, 2980–2913.

Kuhl, D. E., Hale, J. & Eaton, W. L. (1966), "Transmission Scanning: A Useful Adjunct to Conventional Emission Scanning for Accurately Keying Isotope Deposition to Radiographic Anatomy," Radiology 87, 278–284.

Kuhl, D. E. & Edwards, R. Q. (1964), "Cylindrical and Section Radioisotope Scanning of the Liver and Brain," Radiology 83(5), 926–936.

Kuhl, D. E. & Edwards, R. Q. (1966), "Perforated Tape Recorder for Digital Scan Data Store with Grey Shade and Numeric Readout," Journal of Nuclear Medicine 7, 269–280.

List Continued on next page.

Primary Examiner—Craig E. Church
Assistant Examiner—John C. Freeman
Attorney, Agent, or Firm—Cooper, Dunham, Griffin & Moran

[57] ABSTRACT

Disclosed are x-ray machines using fan-beams of x-rays to examine sectional slices of patients and to form detailed x-ray pictures of such slices, and methods of so examining patient slices. A source of a fan-beam of x-radiation, and a system detecting the radiation after it passes through a slice of the patient, rotate around the patient.

73 Claims, 15 Drawing Figures

OTHER PUBLICATIONS

Kuhl, D. E. & Edwards, R. Q. (1968), "Digital Techniques For On-Site Scan Data Processing," Fundamental Problems In Scanning, Charles C. Thomas, Springfield, Illinois, pp. 250-266.

Kalos, M. H., Davis, S. A., Mittelman, P. S., Mastras, P. & Hutton, H. H. (1961), "Conceptual Design of a Vapor Volume Fraction Instrument," Nuclear Development Corp. of America, White Plains, N.Y., NDA 2131-34, Contract AT (30-1)-2303(IX), U.S. Atomic Energy Comm., 31 pages.

Radon, Johann, Uber die Bestimmung von Funktionen durch ihre Integralwerte langs gewisser Manningfaltigkeiten, 1917 Sitzung Vom 262-277, w/informal translation: Determination of Functions by Its Integral Values Along Various Defined Manifoldnesses.

Bracewell, R. N. & Roberts, J. A. (1954), "Aerial Smoothing in Radio Astronomy," Australian Journal of Physics 7(4), 615-640.

Bracewell, R. N. (1956), "Strip Integration in Radio Astronomy," Australian Journal of Physics 9(2), 198-217.

Bracewell, R. N. (1964), "Reducing Fan Beam Data," Radio Astronomy Institute, Stanford University, Glint No. 76, Mar. 9, 8 pages.

Bracewell, R. N. & Riddle, A. C. (1967), "Inversion of Fan-Beam Scans In Radio Astronomy," Astrophys. Journal 150(2), 427-434.

DeRosier, D. J., Klug, A., Reconstruction of Three Dimensional Structures From Electron Micrographs, 217 Nature 131 (1968).

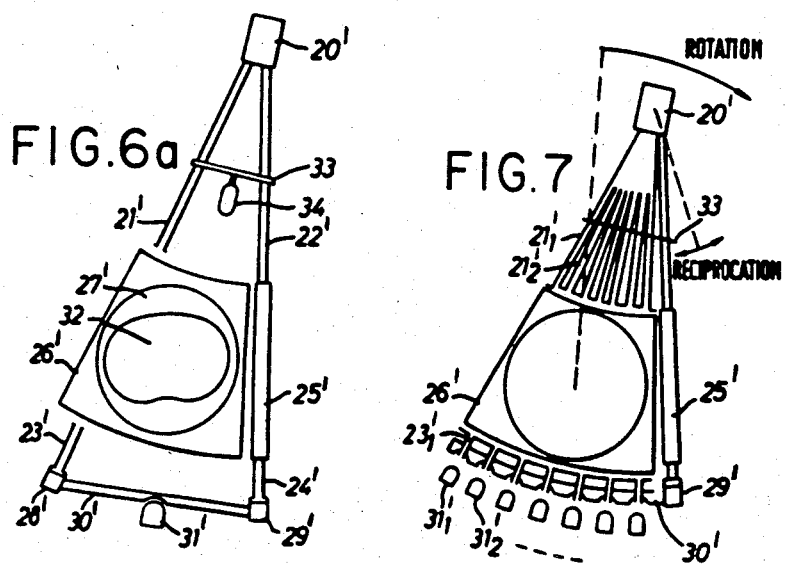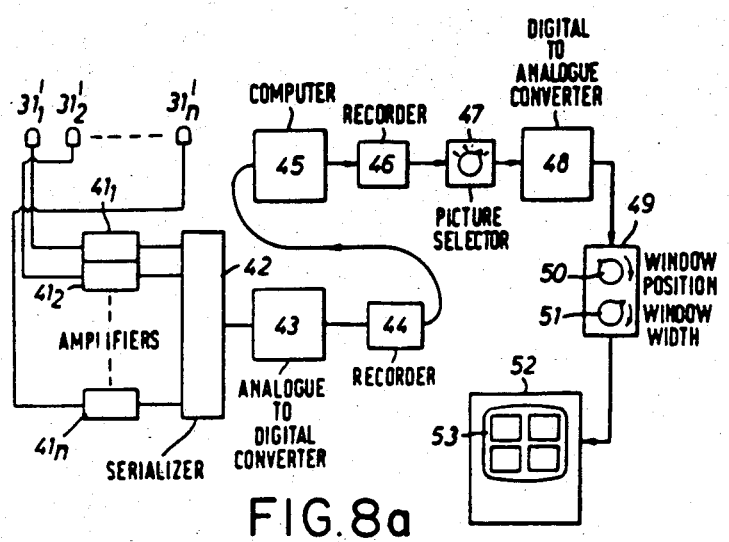

RADIOGRAPHY

REFERENCES TO RELATED APPLICATIONS

This is a continuation of application Ser. No. 013,476, filed Feb. 21, 1979 and a continuation of co-pending parent application Ser. No. 858,612 filed Dec. 8, 1977, now U.S. Pat. No. 4,188,541 and Ser. No. 869,711 filed Jan. 16, 1978. In turn, parent application Ser. No. 869,711 is a continuation of application Ser. No. 758,147 filed Jan. 10, 1977 (now abandoned), which in turn is a continuation of application Ser. No. 481,443 filed June 20, 1974 (now U.S. Pat. No. 4,035,647), which in turn is a division of application Ser. No. 358,980 filed May 10, 1973 (now U.S. Pat. No. 3,881,110), which in turn is based under 35 USC §119 on U.K. application Ser. No. 23064/72 filed on May 17, 1972. In turn, parent application Ser. No. 858,612 is a division of application Ser. No. 780,971 filed Mar. 24, 1977 (now abandoned), which in turn is a continuation of application Ser. No. 657,543 filed Feb. 12, 1976 (now U.S. Pat. No. 4,052,618), which in turn is a division of application Ser. No. 468,005 filed May 7, 1974 (now U.S. Pat. No. 3,944,833), which in turn is a division of application Ser. No. 349,198 filed Apr. 9, 1973 (now U.S. Pat. No. 3,866,047), which in turn is a continuation-in-part of application Ser. No. 212,778 filed Dec. 27, 1971 (now U.S. Pat. No. 3,778,614), which in turn is a continuation of application Ser. No. 861,358 filed Aug. 21, 1969 (now abandoned), which in turn is based under 35 USC §119 on U.K. application Ser. No. 40,317/68 filed on Aug. 23, 1968. Each of the above-identified related patents and patent applications is hereby incorporated by reference in this application as though the entire specification and drawings of each such patent and patent application are fully set forth in this continuation application.

The present invention relates to radiography and it relates especially to techniques for obtaining information indicative of the presence or absence of anomalies in the interior of a body, despite the presence of other material in the body.

In order that the invention may be clearly understood and readily carried into effect, the same will now be described, by way of example only, with reference to the accompanying drawings, of which:

FIG. 1 illustrates, partly in a plan section and partly in block schematic form, apparatus in accordance with one example of the invention, FIG. 2 shows a section on lines II—II of FIG. 1, FIG. 3 illustrates waveforms explanatory of the operation of the apparatus shown in FIG. 1, FIG. 4 shows, in perspective view, apparatus according to another example of the invention, FIG. 5 shows the apparatus of FIG. 7 in plan view, FIGS. 6a and 6b illustrate diagrammatically two other examples of the invention, FIG. 7 illustrates a modification of FIG. 6a, which constitutes another example of the invention, FIG. 8a illustrates, partly in block form, the apparatus embodying the scanning means illustrated in FIG. 5.

Figure 1:
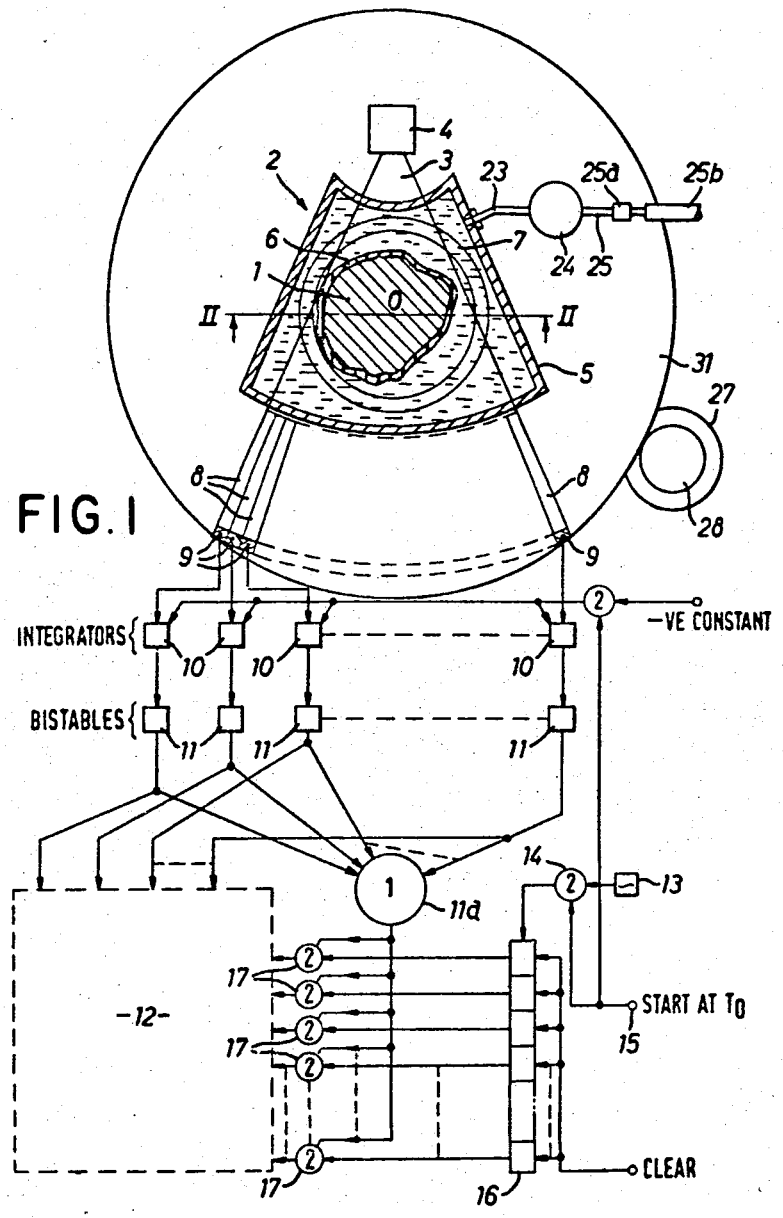
Figure 2:
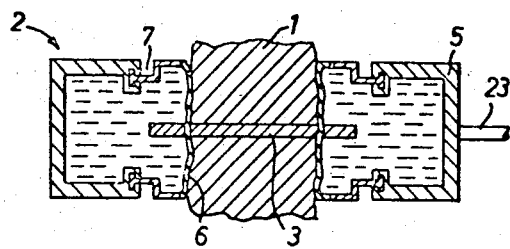

Referring now to the drawings, and more particularly to FIGS. 1 and 2, a body 1 to be investigated is mounted in an arrangement shown generally at 2 so that it can be illuminated by a fan-shaped sweep 3 of penetrative radiation, such as X- or γ-radiation, derived from a source 4.

The arrangement 2, in this example, comprises an enclosure of which the outer walls 5 are formed of the material known by the Registered Trademark "Perspex" or another suitable material. The arrangement is provided with a central aperture in which the body 1 is situated, the aperture being surrounded by a tubular, flexible wall 6 formed, for example, of rubber. The enclosure between the walls 5, 6 is filled with water as indicated by the horizontal shading lines. Water can be pumped into or out of said enclosure means of a pump 24 which is reversible in its operation and which communicates with said enclosure by means of a pipe 23 and with a water reservoir (not shown) via a pipe 25, a closure valve 25a and a removable pipe 25b. Water is pumped out of said enclosure to allow the tubular wall 6 to expand outwardly so that the body 1 can be inserted therein and then water is pumped into said enclosure to cause the wall 6 to fit snugly around the part of body 1 which is to be investigated. In order that the body 1 and the flexible wall 6 may remain stationary whilst the remainder of the enclosure is rotated, a rotary water seal 7 is provided in the arrangement 2. The fan-shaped sweep 3 passes through the arrangement 2 as shown in FIG. 2 and it will be appreciated that the snug fit between the flexible wall 6 and the body 1 must be maintained at least over the area through which the beam passes.

Having passed through the body 1, the fan-shaped sweep 3 is incident upon a plurality of radially extending collimators 8 and the field of view of each collimator defines a respective, discrete path of radiation through the body 1. In one example, 160 such collimators are used. In order that the overall degree of absorption of radiation along each discrete path can be monitored, each collimator 8 communicates with a respective radiation detector 9 which may take one of several forms to be described hereinafter.

Figure 3:
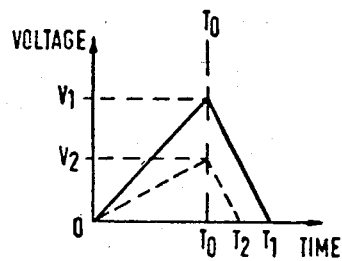

Each detector 9 feeds a respective integrator circuit 10 and the arrangement is such that (referring to FIG. 3) each integrator receives signals from its respective radiation detector for a given exposure period $T_o$. At time $T_o$, a negative voltage is applied in parallel to all the integrators 10 causing them each to discharge towards zero potential. The time taken for the charge held in a given integrator to reach zero potential will clearly be determined by the amount of charge accumulated up to $T_o$, thus if, for example a first detector accumulated charge corresponding to a potential $V_1$ and a second detector accumulated a lesser amount of charge corresponding to a potential $V_2$, the integrator associated with the first detector would reach zero potential in time $(T_1 - T_o)$ whereas the integrator associated with the second detector would reach zero potential in the lesser time $(T_2 - T_o)$. Accordingly, referring again to FIG. 1, each integrator 10 is arranged to feed a respective bistable circuit 11 which is such that it provides an output pulse when the input signal thereto reaches zero potential from a more positive potential. The output pulses from all the circuits 11 pass on the one hand through a common OR gate 11a, and on the other hand as path identity signals to a store 12 associated with a computer (not shown).

An oscillator 13 is arranged to generate regularly occurring pulses at a rapid rate and these are applied to an AND gate 14. The gate 14 is enabled at time $T_o$ by the same control signal as was used to apply the negative potential to the integrator 10, the control signal being applied to a terminal 15, and is arranged to pass the pulses generated by oscillator 13 to a counter 16 continuously from the time $T_o$ to the time when the last of the integrators indicates zero potential.

The counter 16 is a multistage binary counter having sufficient capacity for counting the number of pulses which would be generated by oscillator 13 during the period from $T_o$ to the maximum possible time taken for one of the integrators 10 to indicate zero potential i.e., in the case of zero absorption of the radiation along a given path.

Each stage of counter 16 is connected, via a respective AND gate 17, as a decay time input to the store 12 and the gates 17 are all simultaneously enabled when a pulse derived from any one (or more) of the bistable circuits 11 passes through the OR gate 11a. The store 12 thus receives both path identity and decay time information and the computer is arranged to correlate this information to provide a figure representing the absorption (or transmission) of said radiation along each path. These figures are then covered into logarithmic values and processed, for example in the manner described in the aforementioned U.S. Pat. No. 3,778,614, to provide a representation or a visual record or display of the absorption (or transmission) coefficients of substantially all the elements in a two-dimensional notional matrix of elements defined in the body 1.

In this example, the fan shaped sweep is substantially planar, but it could alternatively be caused to have a greater thickness dimension so as to permit a three dimensional notional matrix of elements defined in the body 1 to be investigated.

In operation, the source 4, the part of arrangement 2 outside the water seal 7, together with the pump 24, pipes 23 and 25 and the valve 25a, from which pipe 25b is then detached, the collimators 8 and the detectors 9 are orbited, about the centre 0 of the arrangement 2, relative to the body 1 in order to expose the body 1 to radiation from a plurality of different directions. For this purpose the aforementioned components are mounted on a turntable 26 which has an aperture therein corresponding to the diameter of the water seal 7, the turntable being driven by means of an electric motor 27 via a suitable drive mechanism 28 which may comprise, for example, a toothed gear wheel adapted to co-operate with gear teeth provided around the periphery of the turntable 16. It is preferable in some circumstances, especially when the human torso is examined, that the aforementioned components be rotated at a rapid rate in order that the irradiation of the torso can be completed sufficiently rapidly that the time available for movement of internal organs of the body (which movement could cause degradation of the resolution of the apparatus) is limited. In these circumstances, it is preferable for the aforementioned components to be rotated continuously rather than step-wise (as described in the aforementioned U.S. Pat. No. 3,778,614). Because of this continuous rotation, each exposure time effectively corresponds to the time taken for the aforementioned components to rotate through a small angle, and in order to reduce or avoid confusion of detail produced by the relative movement between the source and detectors and the body, the computer can be programmed to take account of this.

To evaluate zero for each detector 9 during operation of the apparatus, a shutter (not shown) may be provided between the source 4 and the arrangement 2. This shutter is rotated so that it intermittently interrupts the radiation during each exposure time and the zero reading obtained when the beam of radiation is interrupted is subtracted from the calculated absorption (or transmission) coefficient. The shutter drive mechanism must be synchronised with the mechanism for rotating the aforementioned components of the apparatus so as to enable a zero to be evaluated during each exposure time.

In the apparatus described with reference to FIG. 1, the discharge rate of the integrators 10 is arranged to be linear, and for this reason the binary numbers fed into the store 12 from the counter 16 have to be converted into logarithmic values in order that the overall absorption suffered by radiation traversing the body along a path can be expressed as the sum of the absorptions of the elements of the matrix which are disposed along said path.

An alternative arrangement is to cause the integrators to discharge in accordance with a logarithmic law. When the charge held in an integrator has decayed to a threshold level, the corresponding bistable circuit 11 is arranged to feed a pulse via "OR" gate 11a to the "AND" gates 17. The operation from this point is the same as that described with reference to FIG. 1 except, of course, that the logarithmic conversion has already taken place so that it is unnecessary for the members fed into store 12 from the counter 16 to be so converted.

The threshold level referred to in the last preceding paragraph can be selected to suit individual applications and if a human torso is being examined, the threshold may be made such that an absorption level giving rise to a charge, in an integrator, which decays to the threshold level in a given time $t'$ is allocated a value of zero. Correspondingly, absorption levels giving rise to changes which decay to the threshold level in times less than $t'$ are designated positive (since greater absorption has occurred) whereas absorption levels giving rise to changes which decay to the threshold level in times greater than $t'$ are designated negative.

It will be appreciated that in practice it is convenient for a patient to lie supine with the required part of his torso inside the tubular, flexible wall 6. This can be achieved by arranging the apparatus with its axis of rotation horizontal and by placing suitable couches or the like on either side of the apparatus, the couches being adapted to support, respectively, the upper part and the lower part of the patient's body.

Another example of my invention will now be described with reference to FIGS. 4 and 5 of the accompanying drawings.

Figure 4:
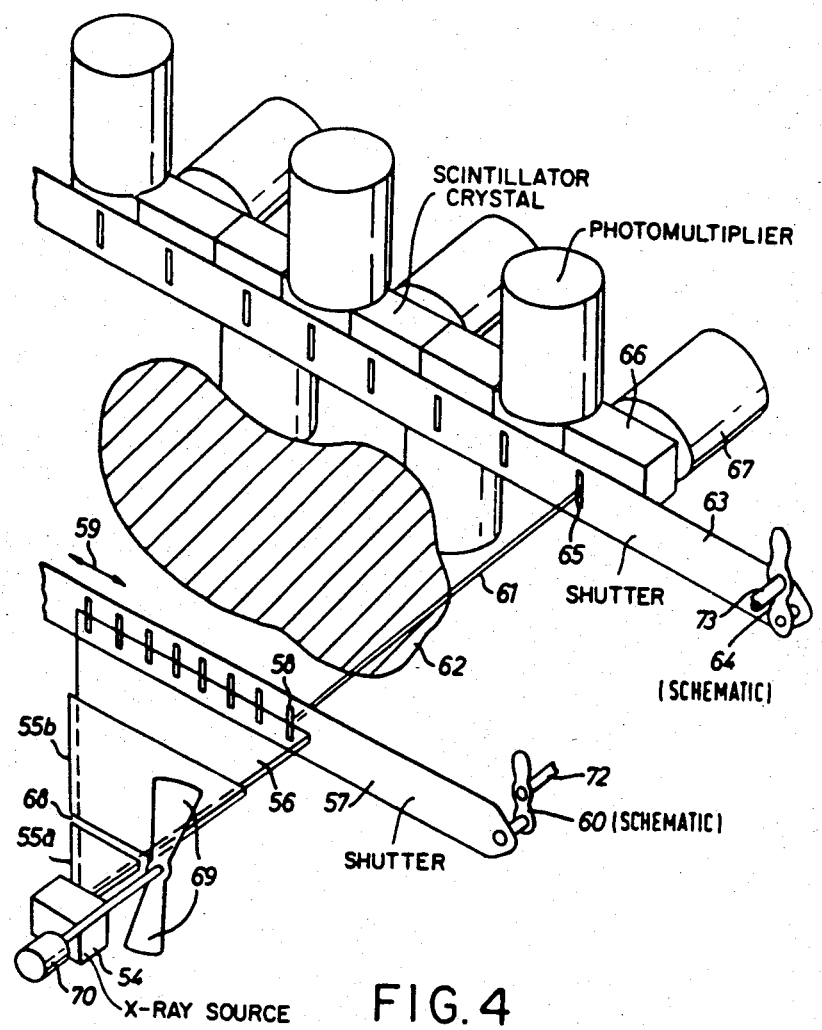

Referring now to FIG. 4 the radiation emitted from an x-ray source 54 is formed, by means of a collimator 55, into a fan-shaped sweep 56. The sweep 56 is incident upon a first shutter member 57 which is constructed of material opaque to the radiation from source 54. The member 57 is formed with a plurality of slit-like apertures such as 58, only eight such apertures being shown in the drawing for reasons of clarity, although in practice many more apertures are provided. The shutter 57 can be moved to and fro, (i.e. reciprocated) in the direction shown by an arrow 59, by means of a motor driven crank arrangement of which a part is shown at 60 in FIG. 4. The said crank arrangement will be more fully described hereinafter.

The radiation passing through the apertures such as 58 when the shutter member 57 is in a given position constitutes a group of equi-angularly spaced rays; the rays of each group being caused to traverse respective paths such as 61 through a region of interest 62.

A second shutter member 63, which is similar to the member 57, is disposed on the opposite side of the region of interest 62 to the member 57. The member 63 is also moveable (by means of a crank arrangement of which part is shown at 64) in the direction shown by the arrow 59 and its motion is synchronized with that of the member 57 so that apertures such as 65 can be aligned with the apertures such as 58 to form, in effect, a second collimating arrangement for the radiation.

Radiation which passes through a given one of the apertures such as 58 and also through the corresponding aperture such as 65 impinges upon a scintillator crystal such as 66, and the visible energy emitted by the crystal in response to the impinging radiation is collected, amplified, and converted into electrical signals by means of a photomultiplier tube such as 67. The electrical signals are processed substantially as described hereinbefore.

It will be observed that the provision of the pairs of spaced apertures such as 58 and 65 enables the radiation to be scanned, in the direction shown by the arrow 59, over the crystals such as 66. This expedient permits a single crystal/photomultiplier to be used for detecting the radiation passing along a respective ray path through the body which scans the sectoral angle between adjacent ray paths defined by the shutter apertures, so reducing (for a given number of paths and groups of paths) the number of crystals and photomultipliers used.

The positions of the two shutter members 57 and 63 are monitored and these determine the ray path along which radiation impinges at any instant on the crystals. Thus, since the same crystal/photomultiplier combination provides an output signal for radiation passing through the region of interest along several different ray paths, it is necessary that the monitored information concerning the positions of members 57 and 63 be taken into account when the computations described hereinbefore are carried out.

It has been found advantageous to make the dimensions of the crystals such as 66 somewhat less than the total amplitude of scan in the direction of arrow 59 so that, as the extremes of scan, some overlap of the radiation upon an adjacent crystal occurs. This allows an extra reading to be taken in the adjacent crystal/photomultiplier combination so that errors due to the junction line of the two crystals can be compensated for. This expedient also provides information to enable one crystal/photomultiplier combination to be matched to the adjacent combination for gain.

The collimator 55 includes a slit 68 which is parallel to the direction indicated by arrow 59, and a shutter 69 is provided as shown so that its blades (which are opaque to x-radiation) can be rotated, by means of a motor 70, into and out of the slit 68 so as to blank off the x-radiation at the extremity of each stroke of the reciprocating motion of shutters 57 and 63. The motor 70 is synchronized with the reciprocating motion in order to achieve the above end.

Figure 5:
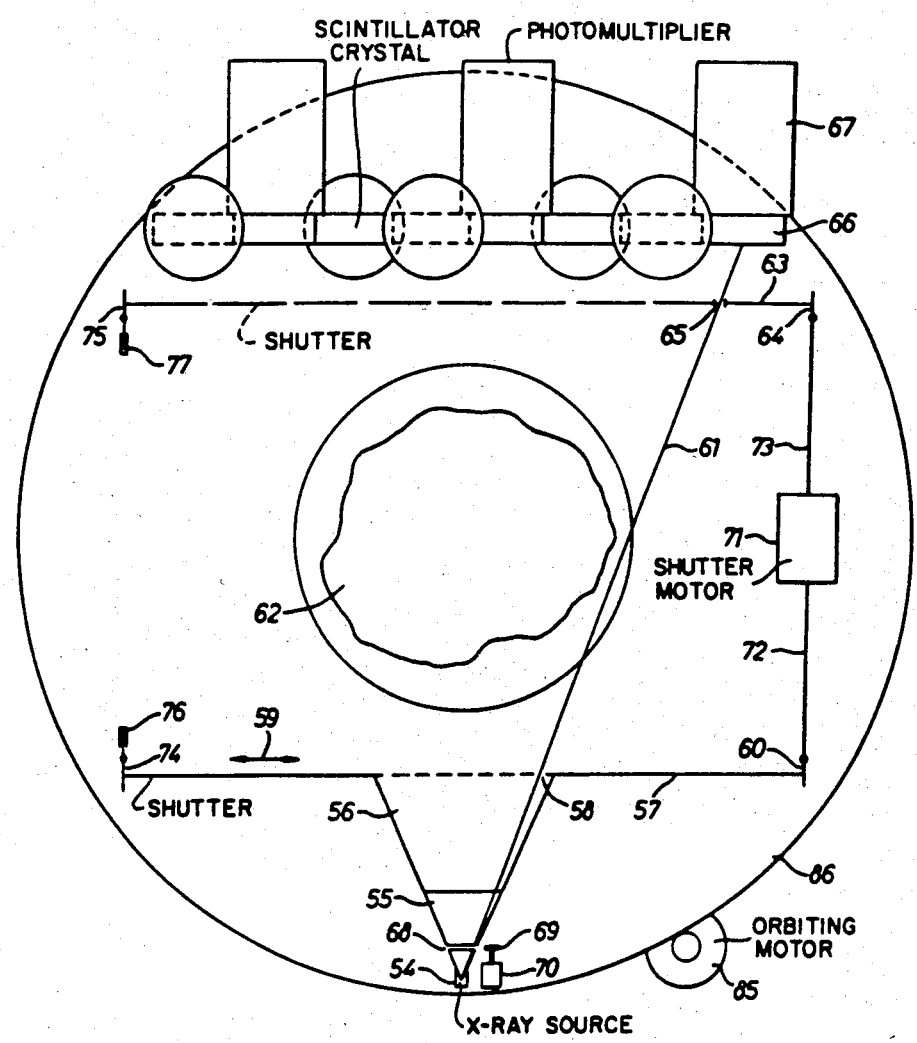

In FIG. 5, features which are similar to features of FIG. 4 have been allocated the same reference numerals. In FIG. 5 the crank arrangement for moving the members 57 and 63 in synchronism is shown in schematic form. It may be seen that the parts 60 and 64 are driven from a common motor 71 via respective couplings 72 and 73. At the left hand ends of members 57 and 63 there are provided respective crank parts 74 and 75 which have shafts which are journalled in bearings 76 and 77 respectively. The motor 71 is preferably a 50 Hz synchronous motor.

Referring again to FIG. 5, the apparatus including the source 54, the first collimator 55, the shutter 69 and its motor 70, the shutter members 57 and 63, the scintillator crystals 66 and the photomultipliers 67 is orbited around the region of interest 62 by means of a motor 85 driving a turntable means 86 on which all of said components are mounted. The motor 85 is preferably synchronized with the reciprocating motion of shutter members 57 and 63 so that each time the shutter members reach an extremity of their travel, the motor 85 is operative to step the turntable around through (say) 1° of rotation. By this means, if all the rays traversing the region 62 at a given angular position of the turntable 86 are referred to as a set of paths, then a corresponding set of paths is traced at each angular position of said turntable. Preferably the turntable is rotated through at least 180° for a given examination.

It will be appreciated that the radiation effects a fan-shaped sweep of the body in a planar slice thereof since the source is a virtual point source in the plane. The source may however have some extent perpendicular to the plane of sweep, since the slice may be relatively thick, or more than one slice may be examined simultaneously. Moreover, in the case where several ray paths are defined by the scanning system, in its rest position, these paths may be parallel, several virtual point sources of radiation then being required.

Referring to FIG. 6a of the drawing there is represented therein an x-ray tube 20' from which the rays, when the tube is operating, pass through two collimators 21' and 22'. The collimator 21' is aligned with a further collimator 23' and the collimator 22' is aligned with a further collimator 24'. Between collimator 22' and 24' is located a dummy attenuator 25'. There is a gap between the collimators 21' and 23' for the location of the object to be x-rayed and in the example illustrated this gap is occupied by a plastics block 26' having a central aperture 27' for the body to be x-rayed. The plastics material may be for example that known as Perspex. Two scintillators 28' and 29' are located at the ends of the collimators 23' and 24' respectively and these communicate via a light pipe 30' with a photomultiplier 31'. A chopper 33 rotatable by an electric motor 34 is arranged to allow beams to pass through the collimators 21' and 22' only alternately to produce scintillations in the scintillators 28' and 29' for detection by the photomultiplier 31'. When the apparatus is in use, the collimators 21' to 24', the attenuator 25', the scintillators 28' and 29', the light pipe 30', the photomultiplier 31', the chopper 33 and the motor 34 are oscillated through the angle subtended by the block 26'. The x-ray source 20' does not take part in this oscillation because it produces a beam wide enough to span the block 26'. However the whole equipment is arranged to rotate slowly about the body to be examined by x-radiation. Such a body is represented by the outline 32.

Figure 6B:
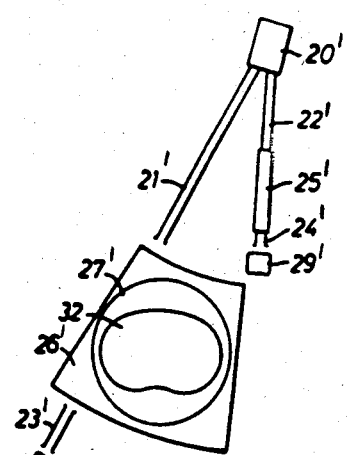

The use of the scintillator 29' and the attenuator 25' provides a reference for the photomultiplier 31'. The material of the attenuator 25 is selected to have similar absorption properties to the body 32 to be examined so that accurate transmission readings may be obtained from the x-radiations which pass through this body substantially independent of the x-ray source intensity. The material in the dummy attenuator 25' compensates, to some extent for the x-ray tube spectrum drift. The space 27' between the body and block 26' is filled with a bag containing water so that the beam intensity received by the scintillator 28' is kept as constant as possible as it traverses the body 32, thus reducing the range of the readings which the photomultiplier 31' has to handle. The apparatus may be calibrated initially by inserting a round homogeneous body in the aperture of the block 26'. FIG. 6b is a similar system but the chopper is discarded and two separate detectors are used for measuring the sources and readings through the body.

The modification of FIG. 6a which is illustrated in FIG. 7 is intended to reduce the time required to complete an examination. According to FIG. 7 a series of photomultipliers $31'_1$, $31'_2$ are used instead of the single photomultiplier 31' of FIG. 6. The photomultipliers have a common reference scintillator 29' and light pipe 30'. Each photomultiplier has individual collimators between it and the source of x-rays 20', the collimators being denoted by the reference $21'_1$ and $23'_1$ in the case of the photomultiplier $31'_1$. With this form of the invention the oscillation of the photomultipliers and the associated collimating systems need be only a fraction of that of the apparatus shown in FIG. 6a. The photomultipliers could also be arranged slightly displaced downwards so that six pictures can be taken at one time. As indicated, in FIG. 8a the outputs of the photomultipliers $31'_1$, $31'_2$ are applied to a series of amplifiers $41_1$, $41_2$ . . . and thence to a serialiser 42 which feeds the plurality outputs of the amplifiers in series to an analogue-to-digital converter 43. The digital output of the converter 43 is fed to a magnetic tape recorder 44 and thence to a digital computer 45 which is programmed to compute the absorption coefficients of the elements of a matr-x notionally superimposed on the body 32 under examination. The coefficients computed by the computer 45 are recorded by a further magnetic tape recorder 56 from which they are applied to a picture selector control device 47. The tape produced by the computer 45 may be replaced on the tape recorder 44, recorder 46 then being unnecessary. The output of device 47 is applied to a digital-to-analogue converter 48 and thence to a control circuit 49 which has a manual knob 50 for controlling the position of the contrast window and another manual knob 51 for controlling the width of the window. The output of the control circuit 49 is fed to a display unit 52 which includes a cathode ray tube having a screen 53. The display unit 52 is arranged to respond to the output signals of the digital computer to build up a visual representation of the section of the object under examination. The term "window" denotes the range of signal amplitudes which is applied to the unit 52 to form the display, and the unit 52 is thus such that different absorption coefficients can be displayed on a scale from black to white. The contrast window width control knob 51 enables the full scale black to white to be occupied by a small or large critical range of absorption coefficients, and the observer may vary the position of the window by manipulation of the control knob 50.

Figure 9:
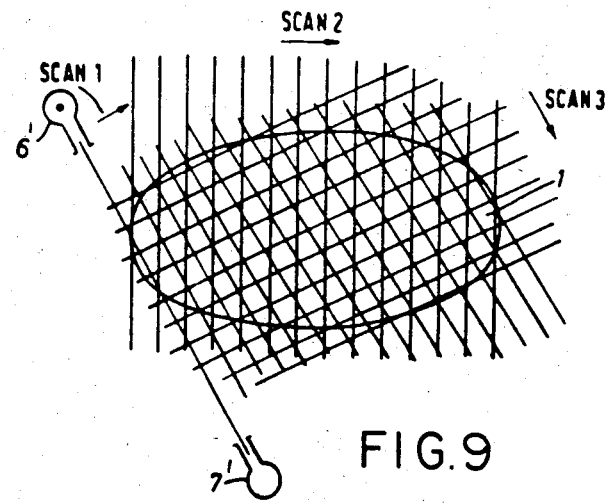
FIG. 9 shows one method of scanning.

FIG. 9 illustrates another type of scanning. Source 6' may be a source of gamma rays but is preferably a source of x-rays. It produces a beam of small cross-sectional area or a ray as it might also be called, for example 3 mm. square or diameter, and preferably includes a collimator to reduce scatter of the rays. A detector 7' may be a scintillator and a scintillation counter and preferably also includes a collimator. The body 1' is scanned by the beam in one plane only, the plane being 3 mm. thick in this example, in a direction not only linearly across the plane, but at a plurality of angles around the plane, the detector 7' being so mounted that it is always pointing toward the source 6'. If only a single scan across the plane were performed, the result would merely be equivalent to a conventional x-ray picture of that plane, all the objects on a line between source 6' and detector 7' being superimposed. However, by performing a large number of scans, sufficient information can be derived to enable the coefficient of absorption of the material in each 3 mm. cube of material in the plane to be calculated and the coordinates of its position in the plane determined. Although only three scans are shown in FIG. 9 it will be appreciated that many more would be required in practice.

In each position of the beam the detector 7' determines the transmission of the x-radiation by a path of relatively small cross-sectional area through the body. The plane under examination is regarded as a two-dimensional matrix of elements and the directions and numbers of paths are such that each element of the matrix is intersected by a group of paths, which paths intersect different groups of elements.

Successive parallel planes may be examined in this way, and a picture of each planar slice used to build up a picture of the entire body or a larger section of it. The slices may be examined in sequence or simultaneously by using a number of x-ray sources and detectors in parallel.

Figure 10:
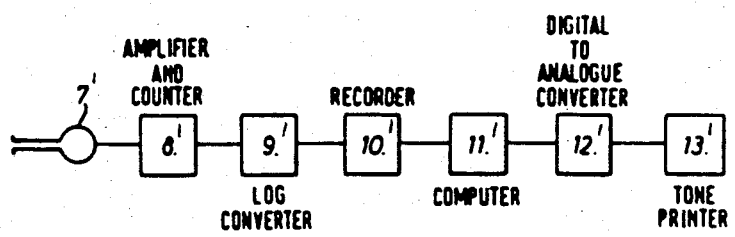
FIG. 10 shows in block form suitable apparatus for use with the apparatus of FIG. 9.

FIG. 10 shows a block diagram of the apparatus producing pictures based on the outputs from detector 7'. The output from detector 7' is applied to an amplifier and counter 8' which produces a digital output representing the number of counts in each reading. The output from 8' is converted to logarithmic form at logarithmic converter 9' whose output is stored in a punched tape or magnetic tape recorder 10 before being transmitted to a digital computer 11' for processing. The computer 11' produces for each 3 mm. cube of a planar slice of body 1' a digital number representing the absorption coefficient of the material within that cube. These digital numbers may be converted to analog form in digital-to-analog converter 12' and applied to a tone printer 13' to produce a picture. Alternately, the computer outputs may be retained in digital form for comparison by pattern recognition techniques, with other digitized pictures.

To achieve the required result, the absorption along each path is deduced from the transmission by each path and a knowledge of the initial intensity of the beam or ray entering each path. The logarithmic converter 9' is used to provide a linear output so that the total absorption along a path is equal to the sum of the absorption in each small element along the path. Let 100 parallel paths be used for each 400 directions spaced equally over 180°. The computer 11' has then 40,000 figures to process, each representing the total absorption along a given path. Consider the section divided into 100×100 similar meshes as on Cartesian graph paper. Each mesh represents an element of the body, but the term mesh will be used in the following mathematical consideration for convenience. The computer 11 is then programmed to give the absorption for each of the 10,000 meshes.

Consider a ray which passes through a set of n=100 meshes through none of which a ray has previously passed. Let the total absorption be Z dB. The computer then allocates a provisional value of Z/100 to each of the meshes. Now suppose that, at a later stage, a ray passes through another set of 100 meshes the absorption in some or all of these meshes having already been allocated. Let the sum of the figures already allocated be $Z_1$ whereas the new measurement gives a total absorption $Z_2$. It will be appreciated that $Z_1$ constitutes a reconstruction of the output signal $Z_2$ derived from the last approximation to the total absorption of the respective meshes. Then a correction $(Z_2-Z_1)/100$ is added to the figures already appearing in each of the meshes. This process is then continued for all the 40,000 rays. This process gives a rough approximation, but to obtain better accuracy, the computer must repeat it a number of times, say five.

Consider a single set of rays all parallel to the y-axis and spaced equally by intervals delta x. The rays are arranged to have a width rather greater than delta x so that some overlapping occurs. The optimum beam width is determined empirically. For mathematical purposes the change of absorption through any interval delta x is assumed to be negligible. We now suppose that the section of the body to be examined is bounded on two sides by the x- and y-axes and is square in shape so that it can be divided into M elementary squares with edges parallel to the axes.

The complete total of rays can be divided into sets each of which consists of parallel rays or effectively parallel rays at a given angle or mean angle. The sets of discrete output signals derived from the rays in each set are treated in the computer in sequence. However, since there are only 100×100 measures and about 400 angles are employed within 180°, rays at neighboring angles must include some of the same squares and their absorption will not, therefore, be independent. If the sets were therefrom taken in angular succession the lack of independence would clearly lead to a slower convergence than if they were independent.

The computer is therefore arranged, by programming, to take the different angular subsets in a pseudo random order with large angular gaps, of say 40°, between successive sets of rays. The sequence is intended to ensure that every angle is included, but not repeated, within the 400 directions. Rays close together in angle then appear far apart in the computer scanning sequence.

Difficulties arise in finding a system which traces through the picture matrix an equivalent beam or ray as it has been called heretofore which has effectively constant width, and which also includes the correct number of picture elements along its length. Both of these requirements are essential for the accurate computer calculations which are to follow.

Figure 11A:
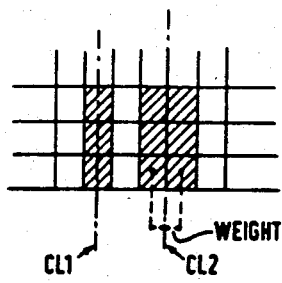
FIGS. 11a, 11b, 11c and 11d illustrate the application of weighting factors to elements of the picture.

The two worst cases are shown in FIG. 11a, where in one case a beam center line CL1 passes through the squares of the matrix perpendicularly and the center line of the beam passes through the center of the squares, in the other case the beam center line CL2 passes between the squares. The latter case would add up to twice as many squares as the former, when the squares along the length of the beam are added up, and would clearly give an error of 2:1.

In order to overcome the above problem the values in each square are multiplied by a weighting factor which is a function of the distance from the center of the square to the center line of the beam, i.e., the squares of beam 2 in FIG. 11a would have a weighting factor of 0.5, the resulting sum of the numbers in the two beams then being equal.

Figure 11B:
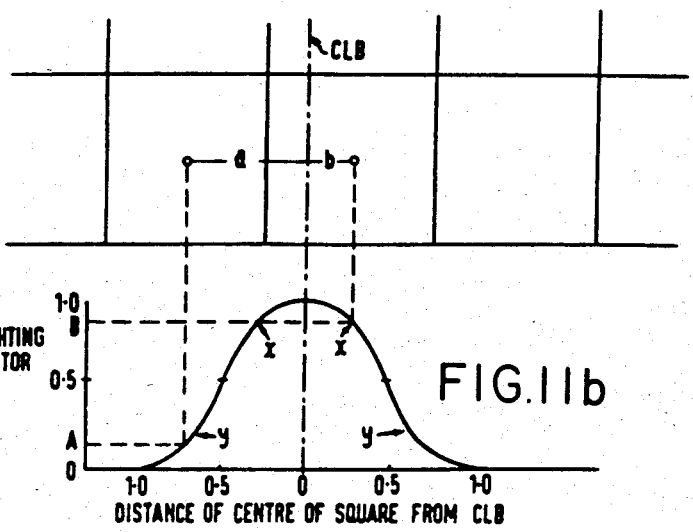

FIG. 11b shows an intermediate position of the beam in which the distances from the center line CLB of the beam to the centers of the two affected squares in the beam are 'a' and 'b' respectively. The corresponding weighting factors 'A' and 'B' can be read off the graph, and when these are added together they must for reasons indicated above add up to unity. Therefore it follows that the parts of the curves labelled 'x' must be drawn the inverse of the parts labelled 'y', if the beam and hence the weighting curve is to be considered symmetrical about its center line.

Figure 11C:
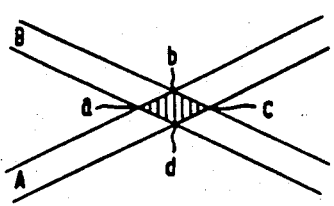
Figure 11D:
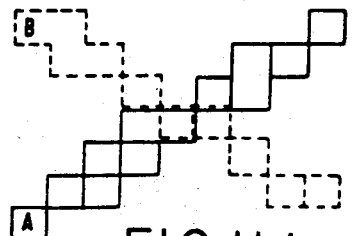

It can be shown that one requirement for accurate summation of values of the matrix squares is idealized in FIG. 11c and its practical equivalent is shown in FIG. 11d using a matrix with a beam at the same angle.

In FIG. 11c the area abcd is obviously constant at any position of the intersection of the beams and is a function of the angle of intersection of the two beams A and B. In FIG. 11d the two equivalent beams vary in width from one to two squares and a constant area at intersection would be impossible without the use of weighting factors. It can be shown that for a given x-ray beam width there is one weighting curve which fulfills all the requirements. For example, if the squares contained at the intersection of the beams in FIG. 11d are multiplied by their respective weighting factors taken from this curve, they will produce a sum which is proportional to the area abcd in FIG. 11c. Any angle of intersection may be chosen and the beam in FIG. 11b may be intersected anywhere along its length for this condition to remain true.

The weighting factor curve can be split up into a table of approximately 20 values to which the computer can refer during calculations without substantially impairing the accuracy of the system.

In some cases it may be more convenient to have a direct display. This could employ a cathode ray tube store for storing the data in analogue form. Preferably, the tube should have large values of screen capacity so that the stored information may be interrogated without causing any significant change in its value. Such tubes are commonly used to provide "bright" radar displays. The summation and computing of values received from the cathode ray tube may be carried out by a simple accumulator and comparator operating a serial mode, and the output fed back to the cathode ray tube to give the necessary small additions to the change built up over the screen. A digital computer would therefore be unnecessary.

Greater detail respecting the machines and methods described above, and respecting variations thereof, can be found in U.S. Pat. Nos. 3,881,110; 3,865,047 and 3,778,614, the specifications and drawings of which have been incorporated herein by reference.

What I claim is:

1. In a method of penetrating ray tomography the steps of:
   directing a divergent beam of penetrating radiation through a body to be analyzed from a source on one side of the body to a detector on the other side of the body;
   effecting a relative angular displacement between the divergent beam of penetrating radiation and the body;

detecting the penetrating radiation that has passed through the body at a number of angularly spaced positions within the angle subtended by the divergent beam for each angular position of the divergent beam relative to the body to derive sets of detected radiation data representative of a plurality of angularly spaced shadowgrams of absorption or transmission of the penetrating radiation by the body, each of said shadowgrams representing the transmission of the penetrating radiation through the body along an array of divergent paths subtended by the divergent beam, and different ones of said sets of angularly spaced sets of shadowgram data corresponding to different sets of intersecting rays of penetrating radiation; and reconstructing the sets of shadowgraphic data into a 3-D tomogram of the body under analysis.

2. In a method of examining at least a part of the interior of a body using penetrating radiation the steps of:

transmitting a divergent beam of radiation from an external source of radiation through the body in a plurality of divergent paths to establish an initial set of divergent ray paths through a generally planar slice of the body;

transmitting divergent radiation from said external source through said body in further sets of divergent paths disposed in said planar slice at different angles from each other and from said initial angle, the sets of divergent rays being such that every element of a two-dimensional matrix of elements of the body in said planar slice is intersected by a group of said rays, the group of rays being different for the different elements of the matrix;

deriving from each ray emerging from the body of a discrete output signal representing the sum of the transmission or absorption of the elements of the body intersected by the ray to derive sets of discrete output signals corresponding to the sets of rays indicative of the transmission or absorption of elements of said matrix; and reconstructing from said discrete output signals a 3-D representation of the transmission or absorption of the elements of the matrix of the slice of the body.

3. In an apparatus for obtaining a 3-D tomograph of a body to be examined:

means for directing a divergent beam of penetrating radiation through the body to be examined from a source on one side of the body to a detector on the other side of the body;

means for detecting the divergent penetrating radiation that is passed through the body at a number of angularly spaced positions within the angle subtended by the divergent beam as a function of the relative angular position of the divergent beam relative to the body to derive sets of detected radiation data representative of sets of angularly spaced divergent ray shadowgrams of absorption or transmission of the divergent penetrating radiation by the body with different ones of said angularly spaced sets of divergent ray shadowgram data corresponding to different sets of intersecting rays of divergent penetrating radiation.

4. The apparatus of claim 3 wherein said radiation detecting means is disposed in the divergent beam path of the penetrating radiation for detecting the divergent radiation after passage through the body; said detecting means including means responsive to the received penetrating radiation for deriving electrical signals representative of the intensity of the radiation as a function of the angular position within the divergent beam of penetrating radiation.

5. The apparatus of claim 4 wherein said means for directing a divergent beam of penetrating radiation through the body to be examined includes, means for directing a divergent fan-shaped beam of penetrating radiation onto the body, said fan-shaped beam of penetrating radiation, as directed onto the body, being of generally continuous uniform intensity across the fan-shaped subtended angle for a given radius from the apex of the fan-shaped beam.

6. The apparatus of claim 5 including, means for radially collimating the penetrating radiation emerging from the body, said collimating means being disposed between the body and said radiation detecting means.

7. In a method of penetrating ray tomography the steps of:

directing a divergent fan-shaped beam of penetrating radiation through a body to be analyzed from a source on one side of the body to a detector on the other side of the body, the divergent fan-shaped beam of penetrating radiation having a generally continuous uniform intensity across the fan-shaped subtended angle for a given radius from the apex of the fan-shaped beam;

effecting relative angular displacement between the divergent beam of penetrating radiation and the body;

collimating the penetrating radiation emerging from the body while maintaining the generally continuous body-attenuated intensity thereof;

detecting the penetrating radiation that has passed through the body at a number of angularly spaced positions within the angle subtended by the divergent fan-shaped beam for each angular position of the divergent fan-shaped beam relative to the body to derive sets of detected radiation data representative of a plurality of angularly spaced shadowgrams of absorption or transmission of the penetrating radiation by the body, each of said shadowgrams representing the transmission of the penetrating radiation through the body along an array of divergent paths subtended by the divergent fan-shaped beam, and different ones of said sets of angularly spaced sets of shadowgram data corresponding to different sets of intersecting rays of penetrating radiation; and reconstructing the sets of shadowgraphic data into a tomogram of the body under analysis.

8. The method of claim 7 wherein the step of effecting relative angular displacement between divergent beam of penetrating radiation and the body comprises effecting said relative angular displacement in a manner which is substantially free of relative lateral translation therebetween.

9. In a method of examining at least a part of the interior of a body using penetrating radiation the steps of:

transmitting a divergent fan-shaped beam of radiation from an external source of radiation through the body in a plurality of divergent paths to establish an initial set of divergent ray paths through a generally planar slice of the body, the divergent fan-shaped beam of radiation having a generally continuous uniform intensity across the fan-shaped subtended angle for a given radius from the apex of the fan-shaped beam;

transmitting divergent fan-shaped radiation from said external source through said body in further sets of divergent paths disposed in said planar slice at different angles from each other and from said initial angle, the sets of divergent rays being such that every element of a two-dimentional matrix of elements of the body in said planar slice is intersected by a group of said rays, the group of rays being different for the different elements of the matrix;

collimating the penetrating radiation emerging from the body while maintaining the generally continuous uniform intensity thereof;

deriving from each ray emerging from the body a discrete output signal representing the sum of the transmission or absorption of the elements of the body intersected by the ray to derive sets of discrete output signals corresponding to the sets of rays indicative of the transmission or absorption of elements of said matrix; and reconstructing from said discrete output signals a representation of the transmission or absorption of the elements of the matrix of the slice of the body.

10. In an apparatus for obtaining a 3-D tomogram of a body to be examined:

means for directing a divergent beam of penetrating radiation through the body to be examined, said means including means for directing a divergent fan-shaped beam of penetrating radiation onto the body, being of generally continuous uniform intensity across the fan-shaped subtended angle for a given radius from the apex of the fan-shaped beam;

means for detecting the divergent penetrating radiation that is passed through the body at a number of angularly spaced positions within the angle subtended by the divergent beam as a function of the relative angular position of the divergent beam relative to the body to derive sets of detected radiation data representative of sets of angularly spaced divergent ray shadowgrams of absorption or transmission of the divergent penetrating radiation by the body with different ones of said angularly spaced sets of the divergent ray shadowgram data corresponding to different sets of intersecting rays of divergent penetrating radiation; and means, disposed between the body and said radiation detecting means, for collimating the penetrating radiation emerging from the body while maintaining the generally continuous body-attenuated intensity thereof as incident upon the radiation detecting means.

11. The apparatus of claim 10 wherein said collimating means radially collimates the penetrating radiation emerging from the body.

12. The apparatus of claim 11 wherein said radial collimator means includes a focused grid collimator having a plurality of collimating vanes for blocking scattered radiation emerging from the body.

13. The apparatus of claim 12 wherein said vanes are directed parallel to the spaced divergent rays emanating from said radiation directing means.

14. The apparatus of claim 10 wherein said means for directing a divergent beam of penetrating radiation through the body includes means for effecting relative angular displacement between the divergent beam of penetrating radiation and the body in a manner which is substantially free of relative lateral translation therebetween.

15. A system comprising:

means for selectively irradiating a sectional slice of a body, means for detecting body-attenuated radiation at respective relative positions of the irradiating means, the slice and the detecting means which define respective raypaths from the irradiating means directly to the detecting means, and means for providing output signals related to the body-attenuated radiation detected for respective raypaths; and means for building up a picture of the slice by accumulating for each elemental area of the picture a succession of contributions each derived by modifying one or more output signals for raypaths passing through or close to the respective elemental volume of the slice which is imaged at said elemental area of the picture on the basis of output signals for other raypaths.

16. A system as in claim 15 in which the number of raypaths for which output signals are provided is at least twice the number of elemental areas of the picture.

17. A system as in claim 16 in which adjacent raypaths overlap in the slice.

18. A system as in claim 17 including means for providing reference signals for making the output signals substantially independent of time variations in the intensity of the irradiating means.

19. A system as in claim 18 including means for displaying the picture by showing at any one time only a window which has a selected width in terms of units of attenuation and is at a selected position on an attenuation scale, and means for selectively changing the window width and position.

20. A system as in claim 19 including means located outside the body for attenuating the radiation progressively more for raypaths which are progressively further from a central region of the slice.

21. A system as in claim 20 in which the body is an inanimate object.

22. A system as in claim 20 in which the body is a living body.

23. A system as in claim 20 in which the body is a human body.

24. A system as in claim 15 in which the radiation irradiating the body at any one time is in the form of a beam collimated to a small cross-section relative to the size of the slice.

25. A system as in claim 24 including means for causing relative scanning motion between the beam and the slice.

26. A system as in claim 25 in which the motion includes relative linear movement between the beam and slice and relative rotational movement between the beam and slice.

27. A system as in claim 26 in which said linear and rotational movements alternate.

28. A system as in claim 27 in which the slice is fixed and the beam moves.

29. A system as in claim 26 in which the body is an inanimate object.

30. A system as in claim 26 in which the body is a living body.

31. A system as in claim 30 in which the body is a human body.

32. A system as in claim 26 in which the adjacent raypaths overlap in the slice.

33. A system as in claim 32 in which the number of raypaths for which output signals are provided is at least twice the number of elemental areas of the picture.

34. A system as in claim 33 including means for displaying the picture by showing at any one time only a window which has a selected width in terms of units of attenuation and is at a selected position on the attenuation scale, and means for selectively changing the window width and position.

35. A system as in claim 34 including means for providing reference signals for making the output signals substantially independent of time variations in the intensity of the irradiating means.

36. A system as in claim 35 including means located outside the body for attenuating the radiation progressively more for raypaths which are progressively further from a central region of the slice.

37. A system as in claim 36 in which the respective contributions to an elemental area of the picture are modified on the basis of the relative spatial positions of the elemental volume and the raypaths passing through or close to the slice.

38. A system as in claim 15 in which the radiation irradiating the body at any one time is in the form of a beam which is wide enough to span the slice.

39. A system as in claim 38 in which the detecting means comprise means for concurrently detecting body-attenuated radiation for a number of raypaths within the beam.

40. A system as in claim 39 including means for causing a purely rotational relative motion between the irradiating means and the slice.

41. A system as in claim 40 in which the slice is fixed and the irradiating means rotate around the slice.

42. A system as in claim 40 including means for causing relative motion between the irradiating means and detecting means.

43. A system as in claim 39 in which the body is an inanimate object.

44. A system as in claim 39 in which the body is a living body.

45. A system as in claim 44 in which the body is a human body.

46. A system as in claim 39 in which adjacent raypaths overlap in the slice.

47. A system as in claim 46 in which the number of raypaths for which output signals are provided is at least twice the number of elemental areas of the picture.

48. A system as in claim 47 including means for displaying the picture by showing at any one time only a window which has a selected width in terms of units of attenuation and is at a selected position on an attenuation scale, and means for selectively changing the window width and position.

49. A system as in claim 48 including means for providing reference signals for making the output signals substantially independent of time variations in the intensity of the irradiating means.

50. A system as in claim 49 including means located outside the body for attenuating the radiation going from the irradiating to the detecting means progressively more for raypaths which are progressively further from a central region of the slice.

51. A system as in claim 50 in which the respective contributions to an elemental area of the picture are modified on the basis of the relative spatial positions of the elemental volume and the raypaths passing through or close to the slice.

52. A system as in claim 15 including means for keeping the irradiating means and detecting means fixed relative to each other and for causing relative scanning motion between the irradiating means and detecting means on the one hand and the slice on the other.

53. A system as in claim 52 in which the scanning motion comprises both relative linear motion across the slice and relative rotational motion around the slice.

54. A system as in claim 53 in which the scanning motion comprises keeping the slice fixed and moving the irradiating and detecting means as a unit.

55. A system as in claim 54 in which the scanning motion comprises alternately moving the irradiating-detecting means unit in linear traverses across the slice and increments of rotational motion around the slice.

56. A system as in claim 15 including means for displaying the picture by showing at any one time only a window which has a selected width in terms of units of attenuation and is at a selected position on an attenuation scale, and means for selectively changing the window width and position.

57. A system comprising:
means for selectively irradiating a sectional slice of a body with collimated penetrating radiation propagating along many different directions and means for detecting radiation leaving the slice and generating output signals related thereto; and
means for building up a picture of the slice through a process in which each of all or substantially all of said output signals contributes to the entire or substantially the entire picture and the entire or substantially the entire picture receives contributions based on one group of said output signals and then receives and accumulates successive contributions based on successive other groups of said output signals.

58. A system as in claim 57 in which each output signal is for a raypath defined by a selected relative position of the irradiating means and detecting means and the body and in which the means for building up the slice picture comprise means for using each given output signal, as modified by selected other output signals, to make contributions to the area of the picture imaging the part of the slice traversed by the raypath giving rise to the given output signal.

59. A system as in claim 58 including means for weighting the contribution to be made to an elemental area of the picture for a given modified output signal on the basis of the distance between the center of the elemental volume of the slice which is imaged at the elemental area and the centerline of the given raypath.

60. A system as in claim 57 in which the irradiating means and detecting means comprise means for concurrently irradiating means a number of detecting devices with body-attenuated radiation and for generating respective output signals from the irradiated devices.

61. A system comprising:
means for selectively irradiating a section of a body with penetrating radiation from many different directions;
means for detecting body-attenuated radiation and for producing signals related thereto for many respective directions;
means for correcting the signals on the basis of contributions from others of said signals to enhance their usefulness for building an accurate picture of the section; and means for building up a picture of the section by cumulatively allocating the corrected signals, or signals derived therefrom, to strip-like portions of the picture which are along the respective directions corresponding to the respective corrected signals.

62. A system comprising:

means for selectively irradiating a sectional slice of a body;

means for detecting body-attenuated radiation at respective relative positions of the irradiating means, the slice and the detecting means which define respective raypaths from the irradiating to the detecting means, and for providing output signals related to body-attenuated radiation detected for respective raypaths; and means for building up a picture of the slice by accumulating, for each respective one of a number of elemental areas of the picture, a succession of contributions derived by modifying output signals for raypaths passing through or close to a respective elemental volume of the slice which is imaged at the respective elemental area of the picture, on the basis of output signals for other raypaths which pass through or close to other elemental volumes of the slice.

63. A system as in claim 62 in which the irradiating means comprise at least one source of penetrating radiation and the detecting means comprise at least one detector of body-attenuated radiation, and including means for selectively causing relative motion between at least the irradiating means and the slice.

64. A system as in claim 63 in which the relative motion comprises traversing and rotating motion.

65. A system as in claim 62 in which the irradiating means and the detecting means are fixed relative to each other to form a unit, and including means for causing relative motion between said unit and the slice.

66. A system as in claim 65 in which one of said unit and the slice is fixed and the other is movable.

67. A system as in claim 66 in which the relative motion comprises traversing and rotating motion.

68. A system as in claim 66 in which the relative motion is solely arcuate.

69. A system as in claim 66 in which the slice is fixed and the unit moves.

70. A system as in claim 62 including means for selectively causing relative motion between at least the irradiating means and the slice which is substantially free of relative linear motion.

71. A system as in claim 70 including means for selectively causing relative motion between the irradiating means and the detecting means.

72. A system as in claim 62 including means for selectively causing relative motion between the slice and the irradiating means and between the slice and the detecting means which is substantially free of relative linear motion.

73. A system as in claim 62 in which the irradiating means irradiates the slice with a fan-shaped beam of radiation which is wide enough to encompass the entire slice.

* * * * *